US012281289B2

United States Patent
Della Toffola et al.

(10) Patent No.: US 12,281,289 B2
(45) Date of Patent: Apr. 22, 2025

(54) METHOD AND APPARATUS FOR CONTROLLING A WINEMAKING PROCESS

(71) Applicant: OMNIA DELLA TOFFOLA S.P.A., Signoressa di Trevignano (IT)

(72) Inventors: Giacomo Della Toffola, Montebelluna (IT); Yacine Amami, Tunisi (TN); Luca Comin, Trevignano (IT)

(73) Assignee: OMNIA DELLA TOFFOLA S.P.A., Trevignano (IT)

( * ) Notice: Subject to any disclaimer, the term of this patent is extended or adjusted under 35 U.S.C. 154(b) by 512 days.

(21) Appl. No.: 16/640,524

(22) PCT Filed: Aug. 10, 2018

(86) PCT No.: PCT/IB2018/056029
§ 371 (c)(1),
(2) Date: Feb. 20, 2020

(87) PCT Pub. No.: WO2019/038626
PCT Pub. Date: Feb. 28, 2019

(65) Prior Publication Data
US 2020/0354658 A1 Nov. 12, 2020

(30) Foreign Application Priority Data

Aug. 25, 2017 (IT) .......................... 102017000096325

(51) Int. Cl.
*C12G 1/02* (2006.01)
*G01N 21/25* (2006.01)
*G01N 33/14* (2006.01)

(52) U.S. Cl.
CPC ............. *C12G 1/02* (2013.01); *G01N 21/251* (2013.01); *G01N 21/255* (2013.01); *G01N 33/146* (2013.01)

(58) Field of Classification Search
CPC .......... G01N 33/146; G01N 21/25–2021/399; C12G 1/02–04
See application file for complete search history.

(56) References Cited

U.S. PATENT DOCUMENTS 8,817,329 B2 * 8/2014 Satoh ...................... G01J 3/524
358/1.9
8,885,934 B2 * 11/2014 Lings .................... G01J 3/0264
382/167

(Continued)

FOREIGN PATENT DOCUMENTS

| CL | 2014001629 A1 | 1/2015 |
| EP | 1205752 A1 | 5/2002 |
| FR | 2347438 A1 | 11/1977 |

OTHER PUBLICATIONS

Capitán-Vallvey, L.F. et al, "Recent developments in computer vision-based anaytical chemistry: A tutorial review," Analytica Chimica ACTA, vol. 899, Oct. 23, 2015, pp. 23-56.

(Continued)

*Primary Examiner* — Violeta A Prieto
(74) *Attorney, Agent, or Firm* — Fredrikson & Byron, P.A.

(57) ABSTRACT

A control method and an associated apparatus for a winemaking process, wherein a must obtained from the pressing step is sent to one of a plurality of fermentation tanks or a must is taken from a maceration and fermentation tank. The method comprises the steps of: —preselecting at least one colorimetric value of the said must; —colorimetrically measuring the must; —comparing the colorimetric value measured with said preselected value and—in the case of a deviation by a predefined amount between said two values: —sending said must obtained from the pressing step to a second tank different from the one said must was directed to; —stopping the maceration and fermentation of said must (Continued)

taken from the maceration and fermentation tank and transferring it into an aging tank or barrel.

11 Claims, 8 Drawing Sheets

(56) References Cited

U.S. PATENT DOCUMENTS

| | | | | |
|---|---|---|---|---|
| 2002/0025079 | A1* | 2/2002 | Kuwata | H04N 1/4074 |
| | | | | 382/199 |
| 2004/0136604 | A1* | 7/2004 | Kuwata | H04N 1/4074 |
| | | | | 358/1.9 |
| 2005/0110797 | A1* | 5/2005 | Masuda | G01J 3/46 |
| | | | | 345/594 |
| 2012/0288195 | A1* | 11/2012 | Lings | G01J 3/0264 |
| | | | | 382/167 |
| 2012/0294517 | A1* | 11/2012 | Lings | G01J 3/463 |
| | | | | 382/162 |
| 2013/0136349 | A1* | 5/2013 | Lings | G06K 9/6201 |
| | | | | 382/165 |
| 2013/0148885 | A1 | 6/2013 | Lings et al. | |
| 2013/0208289 | A1* | 8/2013 | Satoh | G01J 3/462 |
| | | | | 358/1.9 |
| 2015/0140166 | A1* | 5/2015 | Escudier | C12G 1/0213 |
| | | | | 426/15 |
| 2020/0148982 | A1* | 5/2020 | Della Toffola | A23N 1/02 |

OTHER PUBLICATIONS

Talaverano, M.I. et al., "Effect of early leaf removal on *Vitis vinifera* L. cv. *tempranillo* seeds during ripening based on chemical and image analysis," Scientia Horticulture, vol. 299, Jun. 30, 2016, pp. 148-155.

Alimelli, A. et al., "Direct quantitative evaluation of complex substances using computer screen photo-assisted technology: The case of red wine," Analytia Chimica Acta, vol. 597, No. 1, Jul. 19, 2007, pp. 103-112.

PCT International Search Report and Written Opinion dated Oct. 11, 2018 for Intl. App. No. PCT/IB2018/056029, from which the instant application is based, 14 pgs.

European Patent Office "Communication Pursuant to Article 94(3) EPC" From Application No. EP 18765501.4, Dated Sep. 5, 2024, p. 3.

Skouroumounis et al. "The influence of ascorbic acid on the composition, colour and flavour properties of a Riesling and a wooded Chardonnay wine during five years' storage" Australian Journal of Grape and Wine Research 11, Influence of ascorbic acid on white wine oxidation, Published Aug. 15, 2005, pp. 355-368.

* cited by examiner

TABLE 1 (ROSE' WINE)

| ID | Selected color | RGB of the selected color | Press step | Pressure | Recovered volume (hl) | Time | MEASURED VALUE | CLOSEST PANTONE COLOR | CLOSEST PANTONE RGB | Valve |
|---|---|---|---|---|---|---|---|---|---|---|
| 1 | K9 | 255-175-200 | Filling | 0 | 22.7 | 1 | 255-245-240 | K11 | 255-235-235 | 30% |
| 2 | K9 | 255-175-200 | Filling | 0 | 21.8 | 2 | 255-200-230 | J10 | 255-225-225 | 30% |
| 3 | K9 | 255-175-200 | Pressurization | 0.2 | 6.5 | 5 | 255-225-235 | J10 | 255-227-227 | 30% |
| 4 | K9 | 255-175-200 | Pressurization | 0.2 | 3.6 | 6 | 255-225-245 | J11 | 255-234-245 | 30% |
| 5 | K9 | 255-175-200 | Pressurization | 0.2 | 3.3 | 6 | 255-220-240 | J11 | 255-234-255 | 30% |
| 6 | K9 | 255-175-200 | Pressurization | 0.35 | 4.6 | 7 | 255-215-232 | J11 | 255-234-256 | 30% |
| 7 | K9 | 255-175-200 | Pressurization | 0.35 | 2.8 | 5 | 255-210-230 | J11 | 255-200-235 | 30% |
| 8 | K9 | 255-175-200 | Pressurization | 0.32 | 2.7 | 4 | 255-210-230 | J10 | 244-293-224 | 30% |
| 9 | K9 | 255-175-200 | Pressurization | 0.35 | 3.5 | 7 | 255-190-235 | H10 | 255-175-228 | 30% |
| 10 | K9 | 255-175-200 | Pressurization | 0.33 | 1.8 | 8 | 245-170-240 | H11 | 254-175-255 | 30% |
| 11 | J8 | 255-75-175 | Pressurization | 0.42 | 4.7 | 5 | 255-160-225 | G10 | 254-150-225 | 30% |
| 12 | J8 | 255-75-175 | Pressurization | 0.51 | 3.6 | 3 | 254-130-220 | F10 | 255-125-225 | 30% |
| 13 | J8 | 255-75-175 | Pressurization | 0.5 | 3.2 | 5 | 254-175-225 | F10 | 255-125-225 | 30% |
| 14 | J8 | 255-75-175 | Pressurization | 0.73 | 4 | 5 | 254-110-220 | F10 | 255-101-225 | 30% |
| 15 | J8 | 255-75-175 | Pressurization | 0.6 | 3.55 | 4 | 255-99-200 | E9 | 255-100-201 | 30% |
| 16 | J8 | 254-74-175 | Pressurization | 0.78 | 3.9 | 6 | 255-80-190 | C9 | 255-75-200 | 30% |
| 17 | No selection | | Pressurization | 0.96 | 3.2 | 7 | 255-70-195 | C9 | 255-74-210 | 30% |
| 18 | No selection | | Pressurization | 1 | 2.4 | 6 | 255-60-170 | C9 | 264-60-195 | 30% |
| 19 | No selection | | Pressurization | 1.17 | 3 | 8 | 255-25-165 | B8 | 255-25-175 | 30% |
| 20 | No selection | | Pressurization | 1.2 | 2.2 | 9 | 255-25-175 | B8 | 255-25-175 | 30% |
| 21 | No selection | | Pressurization | 1.35 | 2.7 | 8 | 255-10-190 | A9 | 253-12-200 | 30% |
| 22 | No selection | | Pressurization | 1.4 | 2.45 | 10 | 240-10-185 | A9 | 240-10-185 | 30% |
| 23 | No selection | | Pressurization | 1.56 | 1.7 | 9 | 225-0-190 | C9 | 225-0-190 | 30% |
| 24 | No selection | | Pressurization | 1.6 | 1.4 | 12 | 225-0-180 | B8 | 225-0-176 | 30% |
| 25 | No selection | | Pressurization | 1.72 | 1.05 | 10 | 215-0-175 | B8 | 222-0-176 | 30% |
| 26 | No selection | | Pressurization | 1.8 | 0.6 | 12 | 210-0-185 | Y8 | 201-0-176 | 30% |

Fig. 6A

TABLE 2 (WHITE WINE)

| ID | Selected color | Press step | Pressure | Recovered Volume (hl) | Time | MEASURED VALUE | RGB VALUE DETECTED | CLOSEST PANTONE COLOR | CLOSEST PANTONE RGB | Valve |
|---|---|---|---|---|---|---|---|---|---|---|
| 1 | PMS 374 | Filling | 0 | 29.4 | 30 | 70% PMS 363 + 30% PMS 361 | 96-190-85 | PMS 360 | 96-198-89 | 30a |
| 2 | PMS 374 | Filling | 0 | 10.6 | 50 | 80% PMS 363 + 20% PMS 359 | 160-210-130 | PMS 359 | 96-198-89 | 30a |
| 3 | PMS 374 | Pressurization | 0.2 | 5.3 | 6 | 60% PMS 360 + 40% PMS 359 | 160-205-120 | PMS 360 | 96-198-89 | 30a |
| 4 | PMS 374 | Pressurization | 0.2 | 4.1 | 5 | 100% PMS 366 | 196-229-142 | PMS 366 | 196-229-142 | 30a |
| 5 | PMS 374 | Pressurization | 0.35 | 2 | 7 | 50% PMS 367 + 50% PMS 366 | 163-227-125 | PMS 366 | 196-229-142 | 30a |
| 6 | PMS 374 | Pressurization | 0.41 | 3.2 | 4 | 100% PMS 367 | 170-221-109 | PMS 367 | 170-221-109 | 30a |
| 7 | PMS 374 | Pressurization | 0.4 | 2.8 | 3 | 50% PMS 373 + 50% PMS 373 | 194-233-115 | PMS 373 | 206-234-130 | 30a |
| 8 | PMS 3945 | Pressurization | 0.54 | 6.5 | 10 | 50% PMS 381 + 50% PMS 3 80 | 210-228-93 | PMS 381 | 208-226-93 | 30b |
| 9 | PMS 3945 | Pressurization | 0.6 | 4.8 | 8 | 50% PMS 386 + 50% PMS 387 | 228-237-80 | PMS 386 | 233-237-96 | 30b |
| 10 | PMS 3945 | Pressurization | 0.63 | 3.5 | 5 | 50% PMS 387 + 50% PMS 394 | 230-237-53 | PMS 387 | 234-237-68 | 30b |
| 11 | PMS 3945 | Pressurization | 0.8 | 5.1 | 12 | 100% PMS 394 | 234-237-53 | PMS 394 | 234-237-53 | 30b |
| 12 | PMS 3945 | Pressurization | 0.78 | 2.9 | 7 | 100% PMS 3945 | 239-234-7 | PMS 3945 | 239-234-7 | 30b |
| 13 | | Pressurization | 0.94 | 4.2 | 12 | 50% PMS 3945 + 50% PMS 3955 | 23.-230-10 | PMS 3945 | 239-234-7 | 30c |
| 14 | | Pressurization | 1 | 3.6 | 10 | 100% PMS 3975 | 237-226-17 | PMS 3955 | 237-226-17 | 30c |
| 15 | | Pressurization | 1.18 | 4 | 13 | 50% PMS 3955 + 50% PMS 3965 | 235-223-17 | PMS 3955 | 237-226-17 | 30c |
| 16 | | Pressurization | 1.4 | 3.2 | 12 | 80% PMS 3965 + 20% PMS 3975 | 222-220-16 | PMS 3965 | 232-221-17 | 30c |
| 17 | | Pressurization | 1.59 | 2.8 | 15 | 50% PMS 3965 + 50% PMS 3975 | 200-190-15 | PMS 3965 | 232-221-17 | 30c |
| 18 | | Pressurization | 1.8 | 1.72 | 18 | 30% PMS 3965 + 70% PMS 3975 | 190-180-14 | PMS 3975 | 181-164-12 | 30c |

Fig. 6B

TABLE 3 (RED WINE)

| ID | Selected color | FERMENTATION CYCLE | Time | MEASURED VALUE | CLOSEST PANTONE COLOR | CLOSEST PANTONE RGB |
|---|---|---|---|---|---|---|
| 1 | | Filling | 12 | | | |
| 2 | | Pumping over | 24 | PMS 189 | G8 | 254-150-175 |
| 3 | | Pumping over | 36 | PMS 190 | F7 | 255-125-151 |
| 4 | | Pumping over | 48 | PMS 198 | D6 | 255-75-126 |
| 5 | | Pumping over | 60 | PMS 1788 | B3 | 255-25-51 |
| 6 | | Pumping over | 72 | PMS 199 | Y4 | 200-0-75 |
| 7 | | Pumping over | 84 | PMS 207 | Y4 | 200-0-75 |
| 8 | | Pumping over | 96 | PMS 208 | Y4 | 200-0-75 |
| 9 | | Pumping over | 108 | PMS 209 | Y4 | 200-0-75 |
| 10 | | Pumping over | 120 | PMS 222 | Y5 | 200-0-99 |
| 11 | | Pumping over | 132 | PMS 222 | Y5 | 200-0-99 |
| 12 | MAXIMUM COLORING WITHOUT OXIDATION | Pumping over | 144 | PMS 222 | Y5 | 200-0-99 |
| 13 | | Transfer | 156 | | | |

Fig. 6C

METHOD AND APPARATUS FOR CONTROLLING A WINEMAKING PROCESS

RELATED APPLICATIONS

This application is a 35 U.S.C. 371 national stage filing from International Application No. PCT/IB2018/056029, filed Aug. 10, 2018, and claims priority to Italian Application No. 102017000096325, filed Aug. 25, 2017, the teachings of which are incorporated herein by reference.

The present invention relates to a method and apparatus useful in winemaking processes.

As is well known, the production of wine is distinguished essentially by products (wines) which are obtained by means of red winemaking (fermentation of the must together with pomace and grape pips) and those obtained by means of white and rosé winemaking (fermentation of the must without pomace and grape pips). In the first case the bunches of grapes are destemmed and the berries pressed delicately so as to obtain a must consisting of a mixture of juice and pulp of the berries containing the skin and the substantially intact seeds.

In the second case, instead, the grape berries may be loaded directly into a press consisting of a substantially cylindrical tank provided with an elastic membrane which is arranged at right angles to the horizontal axis of the tank and on the opposite side of which usually air under pressure acts; in this way the berries are subjected to a strong pressure which gradually increases as the membrane expands pressing against the mass of berries, or undergo a more or less long period of maceration in contact with the skins and are then inserted in the press.

During this step other types of press may also be used, such as: presses of the horizontal axis, vertical axis, pneumatic, plate, rotating, discontinuous or continuous type.

In the present description:
"white and rosé winemaking" is understood as meaning the production of wines by means of fermentation of the must in a liquid phase;
"red winemaking" is understood as meaning the production of wines by means of total or partial fermentation of the must together with solids such as skins and in some cases grape pips;
"maceration time" is understood as meaning the solid/liquid contact time before and after fermentation.

Then the must or mixture of must and skins and pips thus obtained undergoes a fermentation step at a controlled temperature, determined by the yeasts which are naturally present as well as yeasts which may be added, in order to transform the sugars contained in the must into ethyl alcohol, carbon dioxide and secondary products (such as succinic acid, acetic acid and other secondary products of fermentation); at the end of this step separation of the lees may or may not be performed in the case of white winemaking by means of transfer into steel containers or wooden barrels, where the wine is left to mature in order to improve its organoleptic characteristics. In the case of red winemaking the product undergoes a pressing step in order to separate the solid from the liquid, and the lees are then separated from the wine obtained once fermentation has been completed.

For the production of white wine or rosé wine (obtained by means of the white winemaking process) the fermentation step involves only the must, separated from the skins and the seeds, while for the production of red wine the fermentation involves the presence of the skins in the must so as to allow extraction from the skins of coloring substances contained in them as well as tannins.

In particular, the production of rosé wine involves lightly macerating the skins in the must or directly pressing them.

In the case of red wine production, the fermentation of the must is performed at a slightly higher temperature, namely 26° C. instead of 18-20° C., and lasts for several days; during this time the skins or pomace which tend to accumulate on the surface (forming the so-called cap) must be periodically pushed towards the bottom of the fermentation tank.

In the case of rosé wines the presence of the skins or pomace in the must during fermentation has a much shorter duration since this serves almost exclusively to provide the wine with its light characteristic color.

On an industrial level the must resulting from the pressing operation is predominantly used. As already mentioned, as the pressing membrane expands, the pressure acting on the berries increases and the juice or must is squeezed out of the berries; it is therefore discharged as a continuous flow which is temporarily interrupted when the pressing cylinder or press is filled again with a new batch of grapes.

As mentioned above, other types of press known per se to the person skilled in the art may also be used.

In particular the must has colorimetric characteristics which differ depending not only on the pressing method but also as on the gradually increasing pressure acting on the pressing membrane.

Hitherto, these color differences have been and still are evaluated by the oenologist only visually and this evaluation is used to make the most important decision, namely how long the must produced by pressing must be transferred into the same fermentation tank (and if necessary also undergo maceration) in order to produce a specific batch and/or quality of wine.

The colorimetric evaluation is also important for identifying any oxidation processes which may greatly affect the organoleptic properties of the wine which is ultimately obtained.

It must be also be considered that the color of a must obtained from grapes even when originating from the same vineyard depends on the year of harvest, the rainfall trend during that year, the weather conditions at the time of harvesting, the external temperature, the acidity and pH, the degree of fragmentation of the berries, the loading time and the storage time. For example, if a long journey is required for transportation from the harvesting site to the processing plant, oxidation processes may already be triggered inside the storage trailer of the tractor—in particular if it is overfilled—with a consequent deterioration in the quality of the must and therefore the wine subsequently produced.

Consequently any data collected and stored with regard to the production of previous years may not be used as such, so that the colorimetric evaluation of the must (in the case of white or rosé winemaking) or the must undergoing vinification and maceration—in particular the pumping-over liquid (in the case of red winemaking)—remains of fundamental importance.

Since, as is clear, the crushing or pressing of the harvested grapes must be performed as soon as possible and since the oenologist or the person responsible for pressing cannot always be present, usually an average colorimetric value is determined so that, when the color of the must differs from this threshold value, the must is deviated to another fermentation tank from where a wine with different characteristics will be obtained.

With constant visual colorimetric monitoring it would be possible to ensure that a large volume of the must is recovered and transferred to the first tank, namely the tank from which the wine with the desired characteristics is obtained, with obvious advantages in terms of production volume and economic value of the resultant wine.

The technical problem considered and solved by the present invention is that of enabling, following preselection of at least one predefined and acceptable colorimetric value of the must, constant inspection of the color both of the must obtained from the pressing step in the case of white winemaking and of the must taken during pumping over from the fermentation tank during said operation in the case of red winemaking, as well as comparison thereof with the at least one preselected value, so that, for as long as a predetermined deviation from the aforesaid at least one preselection value is not detected, in the case of white winemaking supplying of the must to a prechosen fermentation tank is continued, and, in the case of red winemaking, the decision is taken to perform solid/liquid separation and the must is transferred into aging barrels or tanks.

The aforementioned constant inspection is achieved by comparing the detected colorimetric value of the must flow being transferred to fermentation tank in the case of white winemaking, or that of the must during pumping over in the case of red winemaking, with the at least one preselected colorimetric value.

The preselection of at least one colorimetric value is performed with reference to a matrix of colors or "color chart" corresponding to given organoleptic qualities of the wine, said charts being known to the person skilled in the art and being available in the form of a so-called "color pantone".

According to a first embodiment of the method according to the present invention, with reference to white or rosé winemaking, the grapes, after undergoing destemming/crushing, are loaded (immediately or after a variable maceration time without fermentation) into a press from the bottom of which the must is removed and transferred to a fermentation and vinification tank; after prior selection, depending on the characteristics of the wine to be produced, of at least one optimum colorimetric value of the must, said value being expressed in RGB values or equivalent, the must is subjected, before being introduced into the vinification tank, to a continuous colorimetric analysis, the result of which, also expressed in RGB or equivalent values, is continuously compared with said preselected optimum value, maintaining the must flow to a preselected vinification tank until a significant predefined difference between said optimum colorimetric value and said measured colorimetric value is detected.

In the preferred embodiment of this solution of the method according to the present invention, upon reaching the said significant difference in colorimetric value, the must flow is directed towards a second vinification tank which is also associated with a preselected colorimetric value, the supply to said second tank being maintained until the colorimetric value measured has, when compared, a significant difference from said second preselected value, whereupon the must flow may be directed to a third vinification tank.

In the case of rosé wine it may be obtained by means of white winemaking or red winemaking and the previously defined method is valid both in the case where the aforementioned wine is obtained by means of white winemaking and in the case of red winemaking, except that (a) in the press, in addition to the must, the berries and skins of the grapes which have been destemmed/crushed are also present and (b) the preselected colorimetric value(s) belong to the rosé wine sector.

In the case, finally, of red winemaking and maceration in the presence of skins and pips, the continuous colorimetric detection is not carried out on the must from the press but on the liquid which is taken from the maceration and vinification tank and which, as is known, contains not only the must but also the pomace. Preferably the colorimetric measurement is carried out on the pumping-over liquid, while the preselected colorimetric value forms a limit value towards which the must tends during fermentation and maceration, so that, when this variation is no longer present, as indicated by the colorimetric measurement, the operator, who has been duly alerted, takes the decision to perform total or partial separation of the total or partial solid/liquid fractions by means of transfer, giving rise to a red wine of a given quality, or to a fraction of a future red wine produced with different grape qualities, each of which based on the same method resulting in one of said fractions forming the final wine.

In this case, therefore, the preselected value forms the reference value towards which the must undergoing fermentation and maceration tends, being converted into wine.

In turn the apparatus according to the present invention comprises essentially:

a colorimetric measurement cell inserted into the flow pipe for the must obtained from the pressing step in the case of white winemaking or taken from the maceration and fermentation tank in the case of red winemaking and/or maceration, in particular the pumping-over liquid, means for comparison of the colorimetric value detected by said cell with at least one predetermined colorimetric value, selection means, associated with said comparison means, for the preselection of at least one colorimetric value to be compared with said detected colorimetric value, and means for controlling at least one valve, placed downstream of said colorimetric measurement cell, for directing the must flow towards a predetermined fermentation tank (in the case of white winemaking) or for determining transfer of the wine undergoing maceration and fermentation (in the case of red winemaking and/or maceration).

In the preferred embodiment said colorimetric measurement cell consists essentially of a hollow opaque body having a through-flow duct for continuous flow of the liquid to be subjected to colorimetric examination—in the case in question the must from the pressing step or the pumping-over liquid of the red winemaking tank—and a lateral housing for a camera, said camera being in optical communication with said through-flow duct and provided with autonomous means for lighting the recording field, said camera being also in communication with processing means for receiving the recorded images continuously or in a predetermined sequence, and extracting from said images information consisting of three RGB basic colors to be provided to said comparison means.

Before considering in detail the particular aspects of the method according to the present invention a brief description of the apparatus for implementing said method may be conveniently provided with reference to the attached figures in which:

FIG. 6A shows Table 1, showing test results in relation to rose' wine;

FIG. 6B shows Table 2, showing test results in relation to white wine; and

Figure 1:
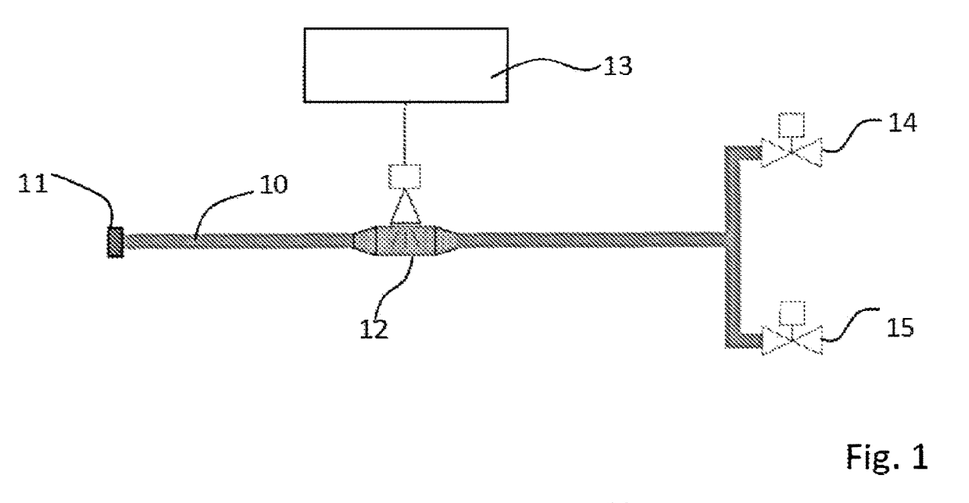
FIG. 1 is a schematic view of the extremely simplified embodiment of the apparatus according to the invention.

With reference firstly to FIG. 1 the reference number 10 denotes a piping, intended for the must flow obtained from the crushing press (in the case of white winemaking) or for conveying the pumping-over liquid of a fermentation and maceration tank (in the case of red winemaking and/or maceration) entering via the end 11.

The reference number 12 denotes overall a colorimetric measurement cell which is crossed by the liquid flow passing inside the piping 10.

The liquid, downstream of the cell reaches a branch-off point where it is deviated to one of the two output valves 14 and 15 which, in reality, may be greater in number (normally three) in the case of white or rosé winemaking.

The reference number 13 denotes a computer workstation, which is designed to receive the signal from the cell 12, said station being provided with a matrix of selectable boxes which represent specific colorimetric values, expressed in units compatible with and therefore comparable with said signal, said station being moreover provided with means for controlling operation of the said output valves 14 and 15.

The valves 14 and 15 control the entry of the liquid inside the respective tank which in the case of white winemaking is a fermentation tank, while in the case of red winemaking and/or maceration it is a tank into which, once the vinification and maceration step has ended, the liquid is transferred for a rest period during which the organoleptic characteristics are refined. As is well known, the transfer tank may be special wooden barrel.

Figure 2:
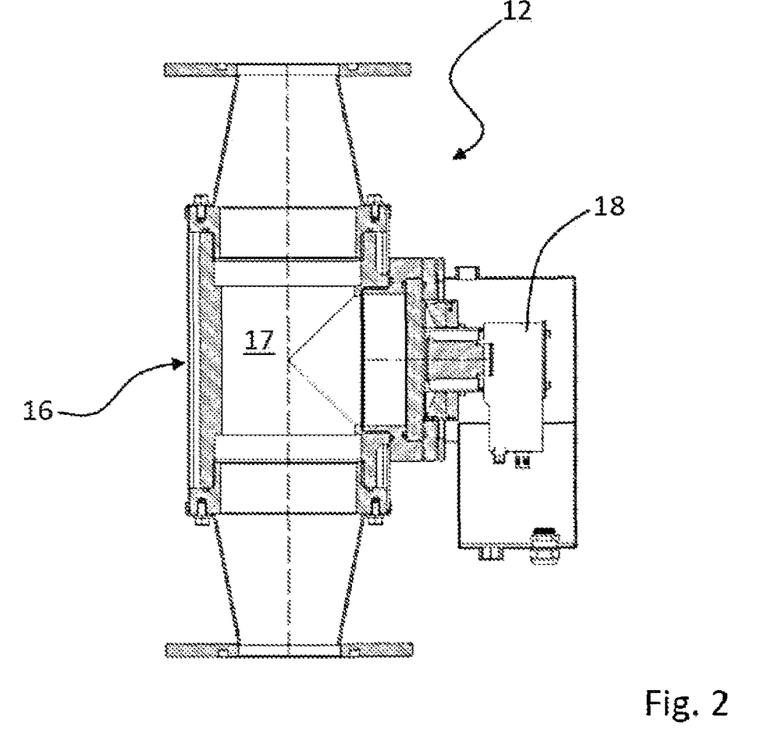
FIG. 2 shows in schematic form a cell for colorimetric measurement of a process liquid.

FIG. 2 shows in greater detail the colorimetric measurement cell which is characterized in that it comprises an external container 16 which has the main feature that it is absolutely opaque to the external light, so as to prevent any interference with the measurement made by the camera housed inside the cell.

The duct 10 in FIG. 1 continues in the form of an axial duct 17 inside the container 16 such that the liquid being examined flows within the recording range of a camera (not shown) which is housed inside a liquid-tight housing 18 provided in a known manner with means for generating light, preferably a flash light, which strikes the liquid flowing inside the duct 17.

The recordings of the camera are performed in a predefined sequence so that images may be taken continuously or at predefined time intervals.

Since the technology in question is known per se to the person skilled in the art, further details are not necessary.

In particular, the pictures are processed in a program, which is also known per se, designed to detect a number of prechosen color components, in particular RGB components (where RGB stands for red, green and blue).

From the above description it is clear that the must which flows inside the duct 10 and therefore inside the duct inside the cell is analyzed in real time, as well as continuously or semi-continuously, so that the measurements which are obtained are simultaneous with the passing of the liquid.

The measurement thus obtained is compared with one or more preselected values, providing an indication for direction of the must flow (in the case of white winemaking) towards a given valve and therefore towards a given tank, until the discrepancy between the two compared values is such that the flow must be directed differently, i.e. towards another valve or another tank.

Figure 3:
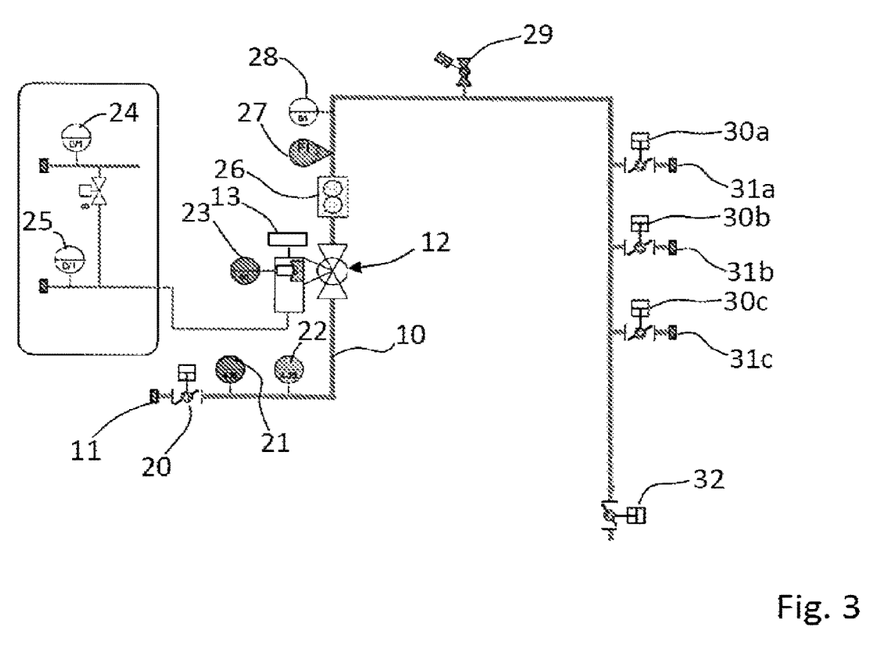
FIGS. 3 and 4 show schematically, in a simplified and complete form respectively, the components and the flow diagram of the apparatus according to the invention.

Considering now FIG. 3, this figure shows the functional components and the flow diagram of the apparatus according to the present invention. In other words, FIG. 3 represents the implementation on an industrial level of the principle illustrated in FIG. 1.

A control valve 20 is positioned at the input 11 for the product (i.e. the must from the crushing press or cylinder or the pumping-over liquid in the case of red winemaking and/or maceration) and downstream of this valve a first inspection of the condition of the product is performed, i.e. the temperature is checked by means of the thermometer 21 and the pressure gauge 22.

The product which flows inside the duct 10 then reaches the colorimetric measurement cell 12, provided with a sensor 23 which signals whether the temperature of the product, in particular the must, is too high for it to be forwarded to the fermentation step. The cell 12 is connected to the already mentioned computer workstation 13. The same cell also receives the signals of two pressure gauges (24 and 25 respectively) which check for the presence of compressed air and pressurized nitrogen. Advantageously the temperature value detected is also used to establish the working conditions of the cell: if the liquid is cold, dry air must be supplied in order to dissolve the condensate, while if the liquid is hot, the air must be supplied in order to cool the cell.

By way of a safety measure, no control members, such as the flow meter 26, haze meter 27 and level sensor 28, must be present so that the product in the supply line from the pressing cylinder or press to the vinification tank is in an optimum condition for ensuring an effective reading by the colorimetric measurement cell.

A valve 29 controls the introduction of pressurized air when is required to empty the circuit.

The duct 10 is then connected to three outputs, i.e. 31a, 31b and 31c, via respective valves 30 (a, b, c), which outputs are in turn connected to respective vinification tanks in the case of must (white winemaking) or to aging tanks or barrels (red winemaking).

Finally, a valve 32 controls the possible emptying of the entire apparatus when required.

Figure 4:
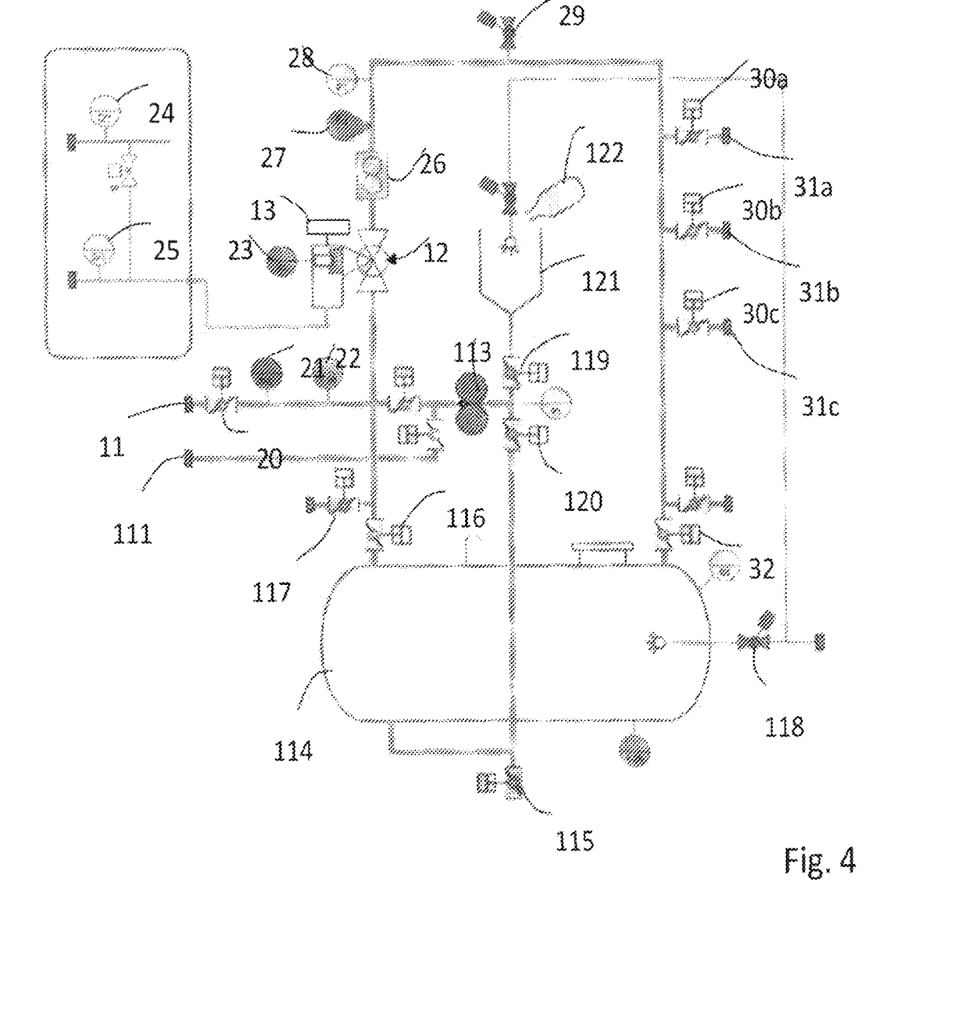

In FIG. 4, the apparatus according to FIG. 3, which represents the operating unit, is shown complete with accessory components.

In particular, a second input 111 for the product is provided, said input being connected via a valve 112 to the intake side of a pump 113, the delivery side of which supplies also the duct 10 upstream of the colorimetric measurement cell.

A service tank 114 is also provided for receiving both the water for washing the various components of the apparatus (the tank is also provided with a suitable service valve 115 for emptying it) and discharge liquids of the riser pipe (via the valve 116) and the downward pipe.

A circuit comprising a tank 121 useful for the preliminary tests is also associated with the pump 113. In this case a sample on which a preliminary colorimetric measurement test is to be carried out is introduced into the tank 121.

The sample is directed from the pump 113 to the duct 10 upstream of the colorimetric measurement cell 12, so that a value to be compared if necessary with preselected values is obtained, The symbol 122 indicates a supply of water for washing the tank 121, said water being then collected inside the tank 114.

As mentioned above, the method according to the invention involves, as a fundamental stage, the comparison of the colorimetric measurement performed in the cell 12 with at least one preselected value.

Figure 5A:
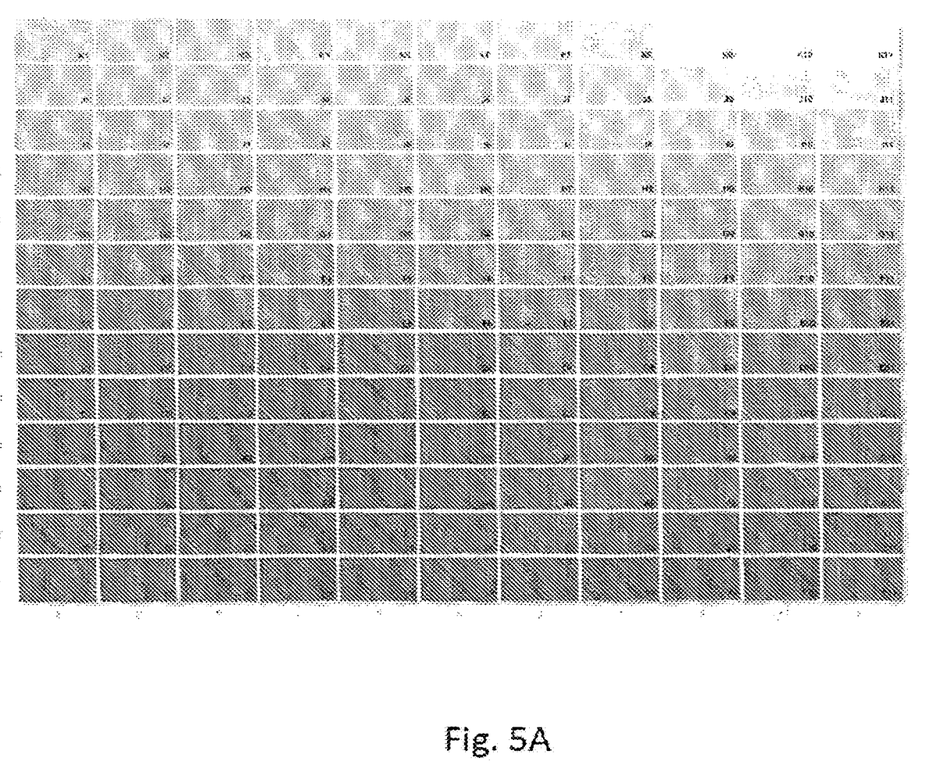
FIG. 5A shows an example of a "color pantone" in the form of a chart relating more specifically to rosë wines.
Figure 5B:
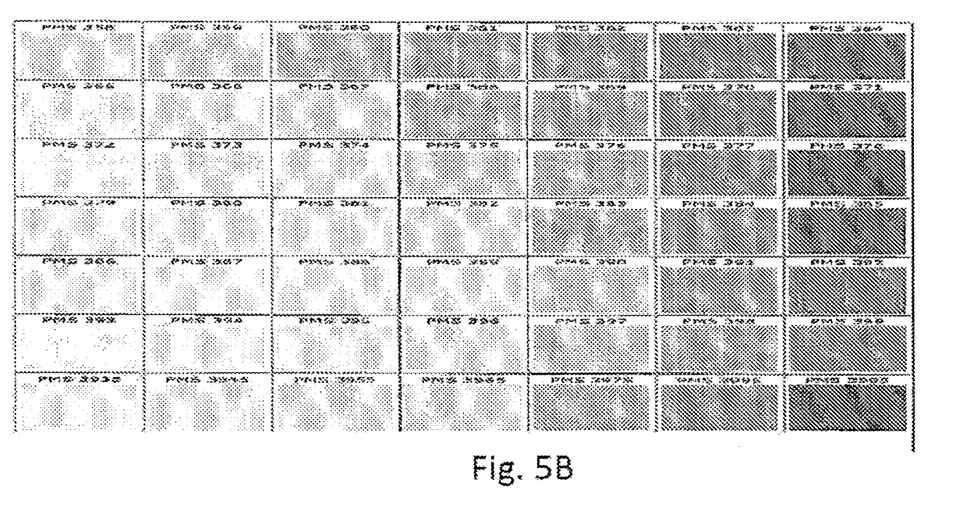
FIG. 5B shows in a similar manner an example of a "color pantone" in the form of a chart relating more specifically to white wines.
Figure 5C:
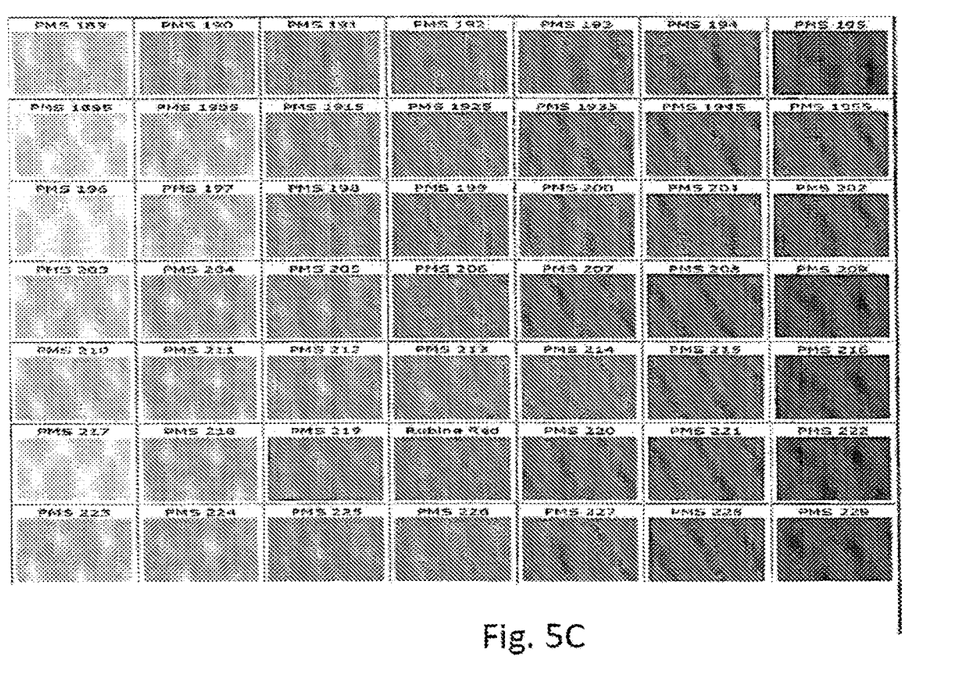
FIG. 5C is a similar view relating more specifically to red wines.

A matrix or color chart, shown in FIGS. 5A, 5B, 5C, is used for the selection.

It is well known that wines, whether they be white, red or rosé, have a characteristic color (which forms in fact one of the evaluative factors when assessing a wine), said color allowing the formation of color charts (well known) in which each box represents a specific color.

In particular, in the case of white wines, the color varies from a more or less dark green to a greenish yellow and even a pale yellow.

The presence of shades of brown is normally an indication that the wine has been exposed (in particular during the initial stages, namely harvesting, destemming, crushing, pressing) to oxidation due to the oxygen in the air. Usually such factors result in a deterioration of the quality.

In the case of red wines the color varies from a pale red to a red which is so dark that it borders on black.

In the case of rosé wines it similarly happens that their color varies from a very pale pink to a very dark pink.

In the case of the must also different colors are detected, these being associated obviously with the characteristics of the starting grapes, so that a white grape produces a must with a very pale green color.

Finally, in the case of red and rosé wines, where the coloring is derived from substances extracted from the skin of the berries or, in the case of some grape varieties, also from the pulp, a gradual increase in the color occurs during vinification.

The coloring changes, in the case of rosé wine, from a very pale pink to a darker pink color and, in the case of red wine, from an initial light red to an increasingly deeper red.

For each grape quality and each type of vinification it is therefore possible to construct a color chart formed by boxes which represent a particular color which may be assumed by the must, upstream of the vinification tank in the case of white winemaking, or by the must undergoing fermentation and maceration in the case of red wine vinification and/or maceration.

As already described, these colors are expressed as three RGB values or other equivalent units.

FIGS. 5 (A, B and C) show examples of these values which may be used in the present invention.

The chart in FIG. 5A is shown in black and white but in reality it is formed by colors ranging from a deep dark red shown in the box indicated by Y11 to a very pale pink color shown in the box K11, while the boxes at the top on the right of the chart show a color varying between pale yellow and pale green and the boxes in the central zone have a color varying between pale pink and deep pink.

In order to allow selection in the apparatus according to the invention, the chart shown in FIG. 5A takes the form of a keyboard in which a pushbutton corresponds to each box. The selection of a pushbutton results in the identification of a well-defined range of RGB components or the like, forming the value with which the result of the colorimetric measurement in the measurement cell 12 is compared, said measurement also being converted into three RGB values or the like.

According to the invention it is also possible to select several boxes and therefore also more than one pushbutton, in which case the colorimetric measurement obtained by the cell 12 will be compared in succession with the values of the selected boxes.

A number of experimental tests applying the method of the present invention have been carried out, said tests confirming the abovementioned advantages as well as other advantages. The tests were carried out in Tunisia in the wine-growing region of Cap Bon, during the harvest of 2016, using four grape qualities, namely:

Sangiovese from the Khanguet region

Marselan from the Grombalia region

Sauvignon blanc from the Rtiba region (vines cultivated close to the coastline).

Example 1—Rosé Wine

In this case the Sangiovese grape variety was used, said grape variety having a potential alcoholic strength of 11.9-12% alc/vol., a tartaric acid acidity of about 6 g/l, with a good sanitary condition of the fruit and a good phenolic maturity.

The harvest was carried out manually at a temperature of about 27° C., using 18-20 kg crates for collecting the grapes.

The crates were then transferred onto a lorry and transported to the processing plant where preliminary selection of the bunches was carried out manually on a conveyor belt.

Sulphating using an amount equal to 4 g per 100 kg of grapes was carried out at the input to the destemmer.

Destemming and crushing was then performed in a machine having a capacity of 15 t/h, to which a pump with a capacity of 15-18 t/h was connected.

The pump was used to supply a press with a throughput of 80 hl (closed cage) having open drainage holes allowing immediate release of the must formed by mere crushing and squashing of the berries.

The press was supplied with dry ice to prevent the grapes coming into contact with the atmospheric air, in this way stopping possible oxidation. Finally pectolytic enzymes were added to the must in the press.

The press was filled continuously with 14 tonnes of grapes.

The must was then introduced into the input end 11 of the apparatus according to the invention.

Table 1 attached to the description shows the results of the entire test.

The color reference value identified in the box H9 of the chart shown in FIG. 5A was firstly selected, this value representing in reality a pale pink color corresponding to an RGB value of 255-175-200.

As mentioned above, the first must subjected to chromatic measurement was the must which runs off during loading of the press.

The first measurement gave an RGB value of 255-245-240. An examination of the chart in FIG. 5A shows that the closest color is that of the box K11 to which an RGB of 255-255-255 corresponds.

This must is clearly directed to the valve 30a, so that it reaches the first vinification tank connected to the output 31a.

In the final part of the filling step, the selected reference value (H9) remaining unchanged, it is possible to detect a variation in the colorimetric measurement of the must which has an RGB of 255-230-230. In this case the box in the chart of FIG. 5A which has the greatest chromatic similarity is the box identified by J10 (RGB: 255-225-225).

From the chart shown in FIG. 5A it can be seen that in the colored form there is an increase in the intensity of the pink color.

When the grape press is then started by applying a pressure it is possible to note a slight variation in the RGB value (from 255-230-230 to 255-225-235), therefore still remaining within the range covered by the box J10.

As the pressing pressure is increased, the measured colorimetric value of the must passing through the cell 12 varies, changing from the box J10 to the box J11 and then to I11, I10 and finally H10 and H11.

This represents the limit where the valve 30a is closed and the valve 30b is opened, so that the must is no longer supplied to the first tank, but to a second tank from where a different quality of rosé will be obtained, with a definitely deeper pink color.

In this case selection of the reference color is performed again, this color being identified in the box D8 of the chart shown in FIG. 5A, said box corresponding to an RGB value 225-75-175.

The measured value of the must has an RGB of 254-160-225 corresponding to the box G10 (RGB: 254-150-225) in the chart of FIG. 5A.

In this case also the trend of the measured RGB values of the must shows an evolution from the color corresponding to box G10 to the color corresponding to box D9.

At this latter value the difference in shade causes closing of the valve 30b (so that the supply to the second vinification tank stops) and opening of the valve 30c, so that via the output 31c a third tank is supplied, a rosé wine with an even deeper shade being produced in said tank.

Alternatively, the residual must following closure of the supply to the second vinification tank could also be discarded, in view of the small amount involved.

From Table 1 it can be seen that in this case a selected color does not exist, but the RGB of the must passing through the cell 12 is merely measured, the measured values showing a rapid variation in the measured color of the must which rapidly approaches the color of the boxes in the chart of FIG. 5 more suitable for red wines and not rosé wines.

Example 2—White Wine

In this case a Sauvignon blanc grape variety was tested, said grape variety having a potential alcoholic strength of 12.4% alc/vol, a tartaric acid acidity of 6.8 g/l, in an excellent sanitary state, with good aging and a green berry color.

The harvest was carried out manually at a temperature of about 24° C., using 18-20 kg crates for collecting the grapes.

After transportation on a lorry the grapes underwent preliminary manual selection on a conveyor belt.

The grapes were subjected to sulphating at the input to the destemmer using an amount equal to to 5 g per 100 kg of grapes.

Destemming and crushing were carried out in a destemmer/crusher with a capacity of 15 t/h served by a transfer pump having a capacity of 15-18 t/h.

The pump was used to perform axial filling of a press with a capacity of 80 hl (closed cage) having open drainage holes which allowed immediate discharging, i.e drainage, of the must resulting from the simple crushing and squashing of the berries.

Dry ice was then introduced in order to prevent contact with the air and stop any oxidation from occurring.

Pectolytic enzymes were then added.

The press was then filled continuously with 13.2 tonnes of grapes.

In this case the reference chart is that shown in FIG. 5B where reference is made to so-called PMS ("pantone matching system") values for tallying with the colors measured as RGB values.

In this case the coloring of the boxes varies from a pale green to a yellowish green and even a brownish green which, however, is characteristic of musts affected by oxidation.

With reference to Table 2 it can be noted that the selected color is that of the box identified as PMS 374 with a light green color.

During the first step, namely that of filling the press, the must which is conveyed into the apparatus according to the invention is that which runs off directly during loading of the press.

The value defined during the measurement in the colorimetric cell 12 is composed in reality of two values, respectively corresponding to PMS 360 and PMS 361, with a measured RGB of 90-190-85.

This in reality is very close to the RGB of PMS 360 which is therefore chosen as reference value.

In FIG. 5B PMS 360 corresponds in reality to a box with a slightly deeper green color than that of PMS 374.

During filling, as can be seen from Table 2, the measured value varies, with a percentage increase of PMS 360 and the appearance of PMS 361 in place of 360. Therefore the situation remains unchanged and the must continues to be sent to the first vinification tank.

Still with reference to Table 2 it can be seen that the start of pressing reduces the component fraction with PMS 360 and then clearly shifts towards PMS 355, 367 and finally 373, where supplying of the must to the first tank stops and the supplying of the second tank via the valve 30b and the output 31b starts.

In this case the reference PMS changes radically assuming a greenish/yellowish color Correspondingly the measured value starts from PMS 381 and increases until it reaches PMS 3945 where supplying of the second tank is stopped and the introduction of the must into the third tank is started.

Example 3—Red Wine

The grape variety used in the test is that of Marselan vine variety (cross between Cabernet Sauvignon and Grenache noir), with a potential alcoholic strength of 12.9-13.2% alc/vol., a tartaric acid acidity of 5.45 g/l, an excellent sanitary condition and a very good phenolic maturity.

The harvest was carried out manually at a temperature of about 29° C., using 20-22 kg crates.

After transportation in a lorry the grapes were preselected manually on a conveyor belt and sulphating thereof carried out using 4 g per 100 kg of harvested crop.

Destemming was carried out in a destemmer with a throughput of 25 t/h, without crushing.

Then the grapes were transferred by means of a pump with a capacity of 25-35 t/h through a coaxial heat exchanger which allowed the temperature of the grapes to be lowered to 18° C.

The grapes were then supplied to a vertical tank of the automatic type with capacity of 300 hl, provided with an automatic pumping-over system, programmable in terms of both frequency and volume. This tank was provided with a jacket for controlling the temperature and a system for automatically unloading the pomace.

After neutralization using dry ice in order to stop oxidation due to contact with the air, the pectolytic enzymes were added.

The tank was filled with 22.5 tonnes of harvested product and at the end of filling yeast was added, with subsequent adjustment of the fermentation temperature to 26° C.

The first pumping-over operation was performed after 24 hours, once the cap had risen, and was repeated every 8 hours using 30 hl for pumping over.

The pumping-over pipe was connected to the apparatus according to the present invention, in order to analyze the increased deepening of the red color, with reference to a predetermined chart, and to signal cessation of the increase in coloring as well as the presence of oxidation factors to which this system is significantly more susceptible.

Figure 6C:
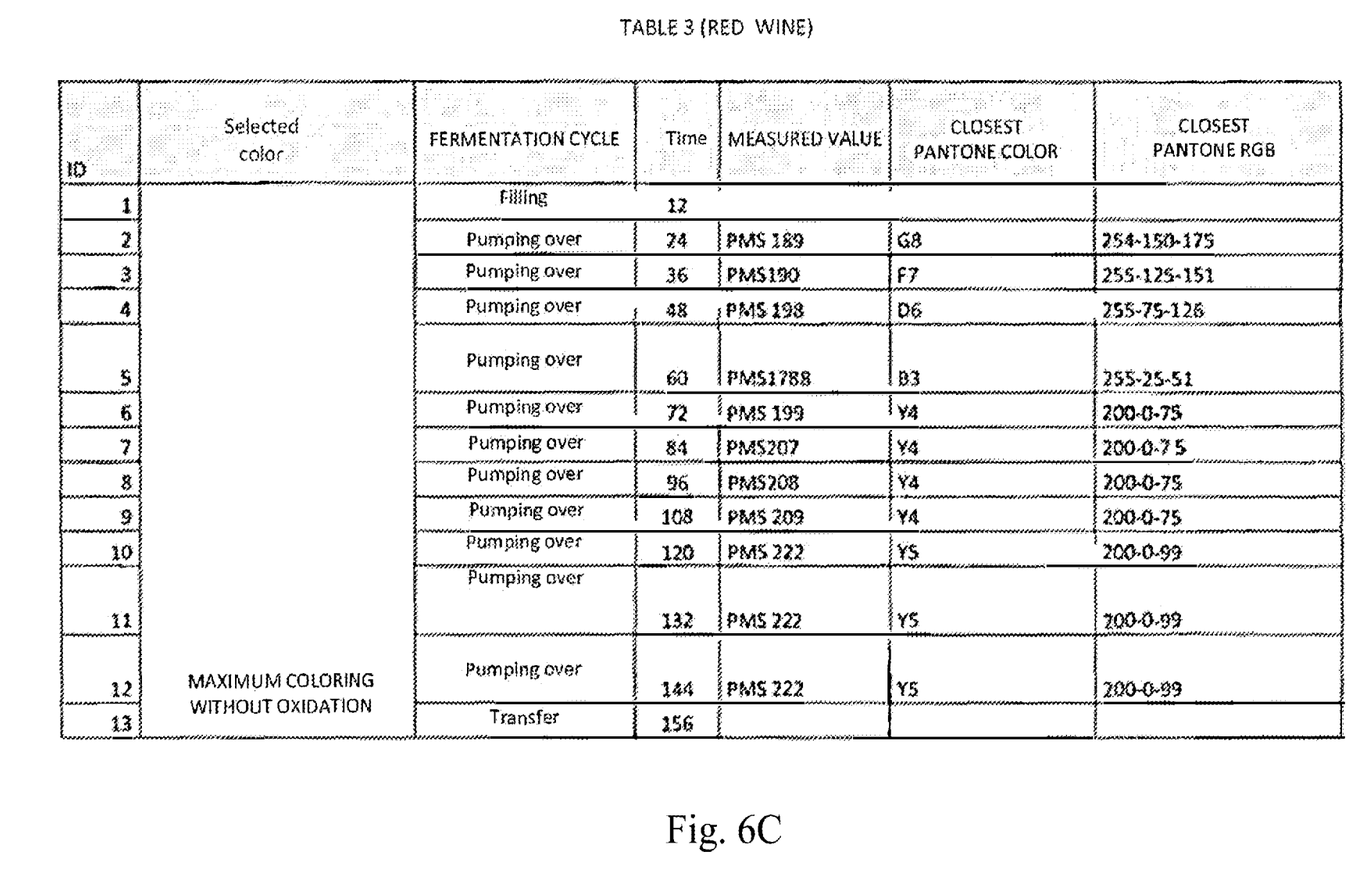
FIG. 6C shows Table 3, showing test results in relation to red wine.

Table 3 shows the progression of this fermentation and how, from an initial colorimetric measurement indicating a closer pantone color corresponding to PMS 189 (equivalent to a light red), a coloring close to the maximum value obtainable (PMS 222) is reached before oxidation occurs, said coloring being optimum for transfer into the aging barrel.

From the above examples and the description the main advantages which can be achieved with the method and the apparatus according to the present invention are evident.

As already mentioned, hitherto it was considered optimum practise to define an intermediate value for coloring of the must (in the case of white or rosé winemaking) and, once that value was reached, to deviate the must into the second vinification tank. This meant that there was a quite considerable loss of must which could have been used in the first tank and therefore a major production loss in terms of top quality wine.

From Tables 1 and 2 it can be easily understood how a major quantity of must is directed towards the first tank.

Secondly the use of the colorimetric comparison between one or more predefined values and the value of the must flow in a continuous or in any case in a programmed manner allows identification with greater precision of the limit beyond which the must flow must be deviated from the first tank to the second tank.

Thirdly, by means of the measured colorimetric values it is also possible to identify in good time the appearance of the first signs of oxidation and therefore take action before vinification is irremediably compromised.

Fourthly and with specific reference to red winemaking, it has become possible to control in a continuous manner the increase in chromatic intensity of the wine during vinification and at the same time signal in good time the moment when this increase ceases, so as to avoid on the one hand the possible occurrence of oxidation and on the other hand perform transfer in good time so that the fermentation and maceration tank is thus made available for further processing.

A further advantage of the present invention consists in the fact that the apparatus can be easily adapted to pre-existing installations and, once put into service, does not require highly qualified personnel for management thereof, thus freeing the oenologist from a task which currently takes up a lot of his/her time.

The invention has been described in relation to preferred embodiments, but it is understood that modifications and variations are possible and are within the competence of the person skilled in the art, so that they fall within the scope of protection of the invention.

The invention claimed is:

1. A method for controlling a winemaking process for the production of wines, comprising the following steps:
    taking a must when producing white or rose wine from a pressing step yet prior to sending the must to one of a plurality of fermentation and vinification tanks, or taking a must when producing red wine from a pumping-over liquid of a maceration and fermentation tank involving maceration and fermentation in the presence of solid which at least includes skins for at least 24 hours;
    preselecting at least one colorimetric value of the said must;
    colorimetrically measuring the must;
    comparing the colorimetric value measured with said preselected value; and
    if a deviation is detected by a predetermined amount between said measured value and said preselected value, either sending said must obtained from the pressing step in the case of white and rose winemaking to a second fermentation and vinification tank different from the one of the plurality of fermentation and vinification tanks to which said must was to be directed, or stopping the maceration and fermentation of said must in the case of red winemaking and transferring said must into an aging tank or barrel;
    wherein the preselecting step of at least one colorimetric value of the said must is performed with reference to a matrix of colors corresponding to given organoleptic qualities of the obtainable wine.

2. The method according to claim 1, characterized in that said stopping of the maceration and fermentation step takes place also when the colorimetric measurement signals a coloration caused by the oxidation of the must due to contact with the ambient air.

3. The method according to claim 2, characterized in that the preselected colorimetric values involves multiple preselected values, in which case the measured colorimetric value of the must is successively compared with each of said preselected values.

4. The method according to claim 1, characterized in that said colorimetric measurement is performed in real time on said must which is made to flow into a colorimetric measurement cell able to take pictures of the must and output a signal which provides colorimetric data of the must expressed in red, green, and blue (RGB) values.

5. The method according to claim 4, characterized in that, when said predetermined deviation occurs, said must is directed to a second fermentation and vinification tank, after preselecting at least one second colorimetric reference value with respect to which a comparison with the measured colorimetric value of the must is performed, the supply to said second fermentation and vinification tank being continued until a predetermined deviation between said second at least one preselected value and said measured colorimetric value arises.

6. The method according to claim 5, characterized in that, upon reaching said deviation of the measured value with respect to said at least one second preselected colorimetric value, the must is deviated towards a third fermentation and vinification tank or is discarded.

7. The method of claim 1, wherein the matrix is predefined depending on type of grapes to be vinified and type of wine to be obtained.

8. The method of claim 7, wherein the matrix is specified from a plurality of matrices each having selectable cells associated with a differing wine type.

9. An apparatus for controlling a winemaking process for the production of wines, comprising:
  (i) a colorimetric measurement cell inserted into a flow pipe for a must either obtained from the pressing step in the case of white or rose wine production or taken from a pumping-over liquid of a maceration and fermentation tank in the case of red wine production; and,
  (ii) a computer workstation connected to said colorimetric measurement cell and comprising means configured for comparison of the colorimetric value of the must detected by said cell with at least one predetermined colorimetric value, said computer workstation being provided with:
    selection means, associated with said comparison means, for the selection of said at least one predetermined colorimetric value comprising a matrix formed by selectable cells each corresponding to a coloring defined by red, green, and blue (RGB) values or equivalent units, each cell being associated with activation means for selection of at least one colorimetric value to be compared with said detected colorimetric value of the must; and
  (iii) means for controlling at least one valve, placed downstream of said colorimetric measurement cell, for directing the must flow towards a predetermined fermentation and vinification tank in the case of white or rose wine production or for determining transfer to an aging tank or barrel of the wine undergoing maceration and fermentation in the case of red wine production;
    said matrix of the selectable cells being predefined depending on type of grapes to be vinified and type of wine to be obtained, the matrix being specified from a plurality of matrices each having selectable cells associated with a differing wine type.

10. The apparatus according to claim 9, characterized in that said colorimetric measurement cell consists of a hollow opaque body having a through-flow duct for continuous flow of the must to be subjected to colorimetric examination, and a lateral housing for a camera, said camera being in optical communication with said through-flow duct and provided with autonomous means for lighting the recording field, said camera being also in communication with processing means for receiving the recorded images continuously or in a predetermined sequence, and extracting from said images information consisting of three red, green, and blue (RGB) basic colors to be provided to said comparison means.

11. The apparatus according to claim 9, characterized in that the preselected colorimetric values are more than one, in which case the measured colorimetric value of the must is successively compared with each of said preselected values.

* * * * *